United States Patent [19]

Cunningham

[11] 4,033,043
[45] July 5, 1977

[54] GAUGE FOR MEASURING LENGTH OF AN OPENING

[76] Inventor: Frank W. Cunningham, 2325 Palos Verdes Drive - West, Palos Verdes, Calif. 90274

[22] Filed: July 9, 1975

[21] Appl. No.: 594,268

[52] U.S. Cl. .......................... 33/143 R; 33/143 C; 33/147 F; 33/174 D
[51] Int. Cl.² .......................................... A61B 5/10
[58] Field of Search ......... 33/174 D, 147 F, 169 B, 33/143 R, 147 K, 148 G, 143 C

[56] References Cited

UNITED STATES PATENTS

| 2,643,459 | 6/1953 | Beer et al. | 33/143 R |
| 3,738,355 | 6/1973 | Salvatore | 33/143 C |

FOREIGN PATENTS OR APPLICATIONS

| 1,149,443 | 4/1969 | United Kingdom | 73/422 |

Primary Examiner—Richard E. Aegerter
Assistant Examiner—Willis Little
Attorney, Agent, or Firm—Fulwider, Patton, Rieber, Lee & Utecht

[57] ABSTRACT

A hand-held gauge for measuring the distance between the near and far edges of an elongated opening in an element, thereby to determine the opening length, and wherein there is access to only one end of the opening. The gauge includes an elongated probe for insertion into the opening. A hook on the probe is operative to engage the far edge of the opening and an elongated member longitudinally slidable upon the probe is adapted to engage the near edge of the opening. A handle is provided to press the probe and elongated member against the opposite edges of the opening, and a measuring scale and pointer are provided on portions of the probe and elongated member to indicate the extent of relative movement between them to thereby indicate the opening length. An interconnection between the probe and elongated member effects engagement of the hook with the far edge of the opening upon initial squeezing of the handle. In one embodiment such initial movement causes the hook to rotate laterally outwardly to hook the far edge of the opening, while in another embodiment such initial movement causes a rod to move up adjacent the hook, filling the opening and thereby preventing the hook from disengaging the far edge of the opening. In either case the result is to securely seat the hook in position prior to engagement of the elongated member with the near side of the opening.

8 Claims, 21 Drawing Figures

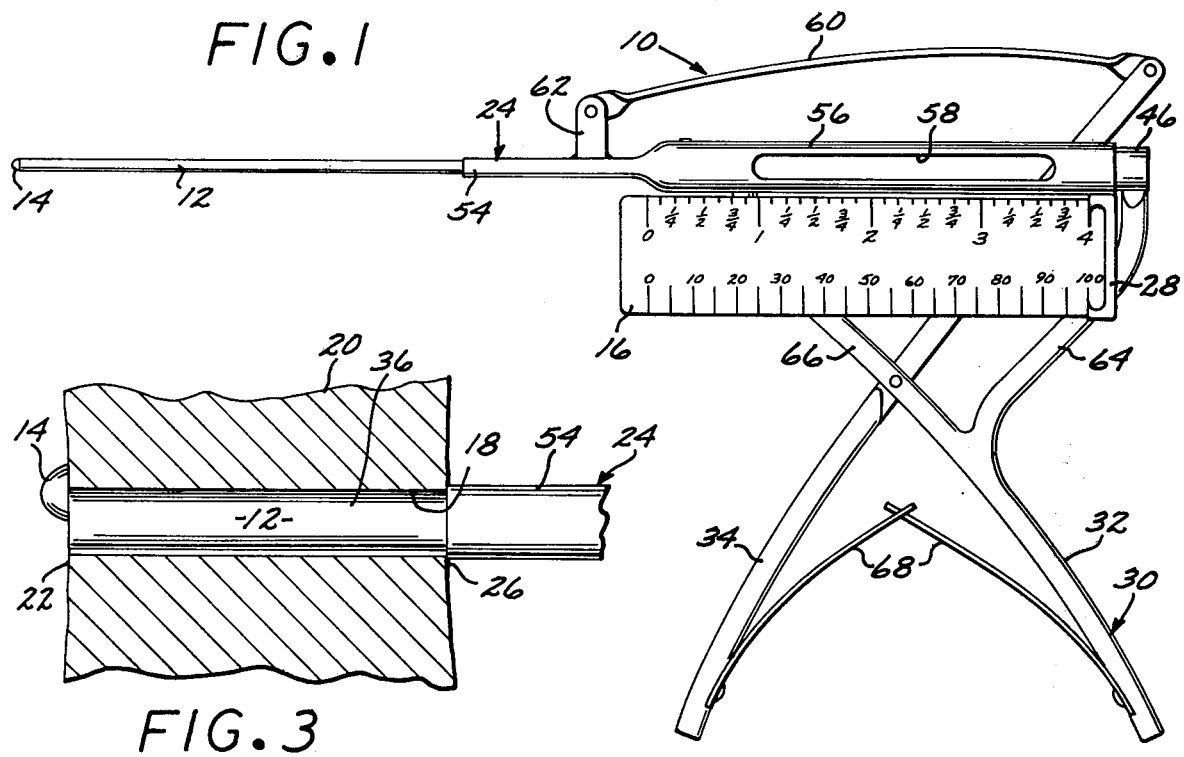
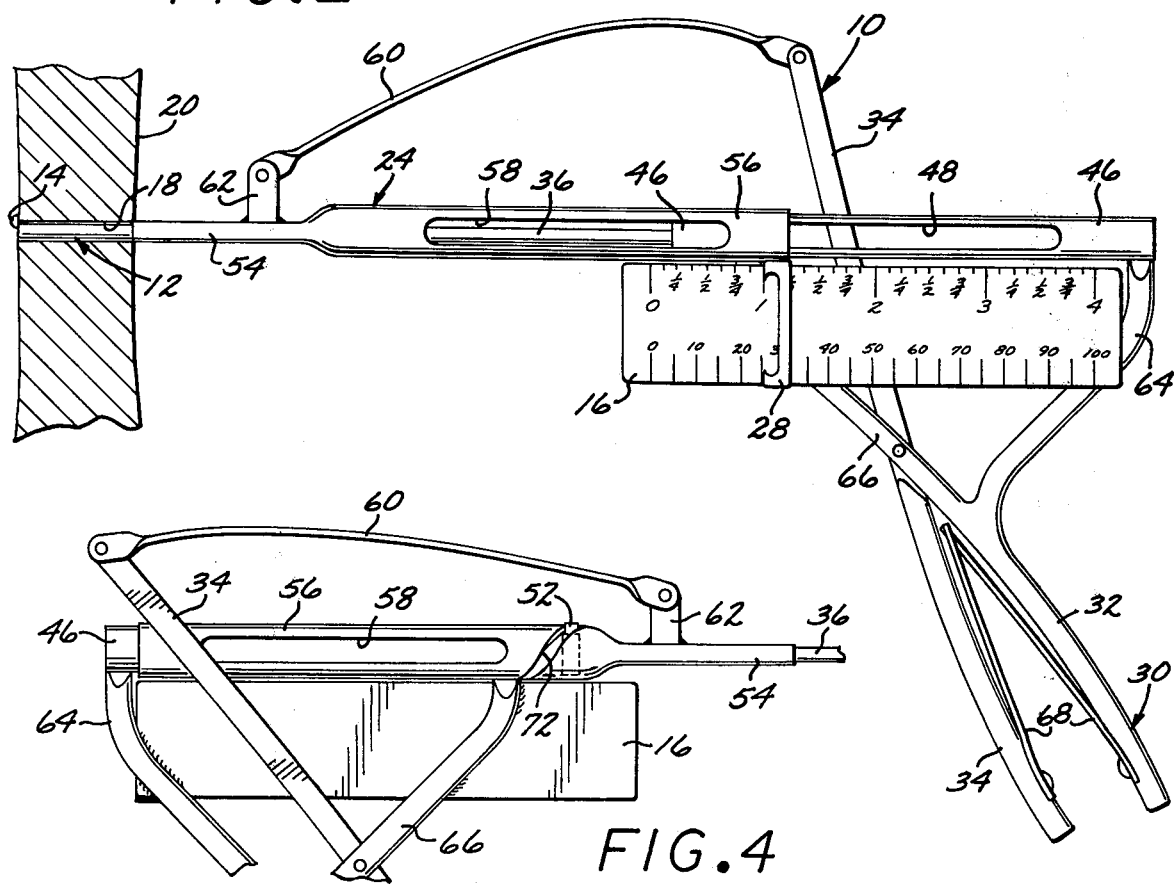

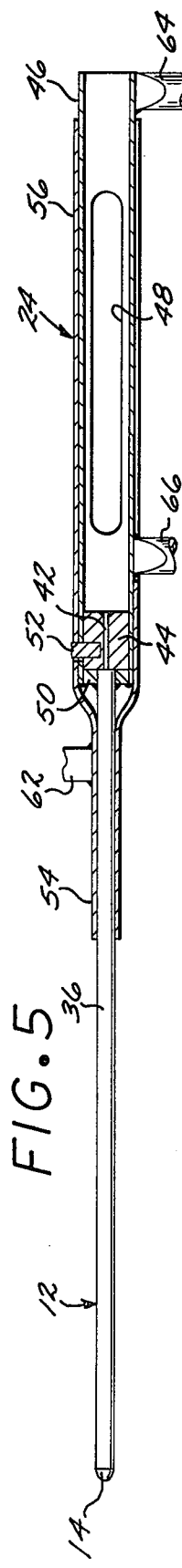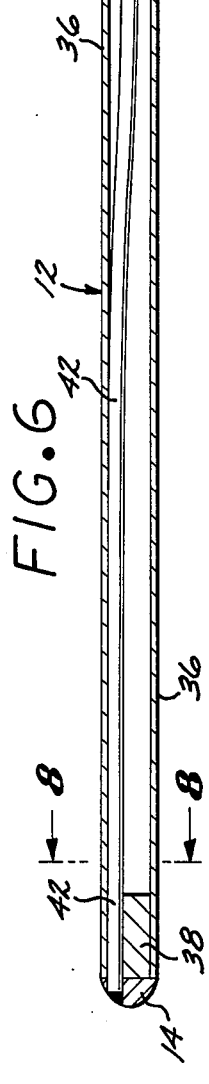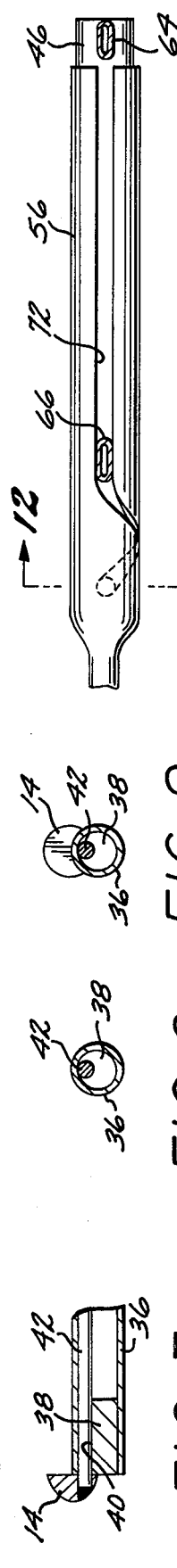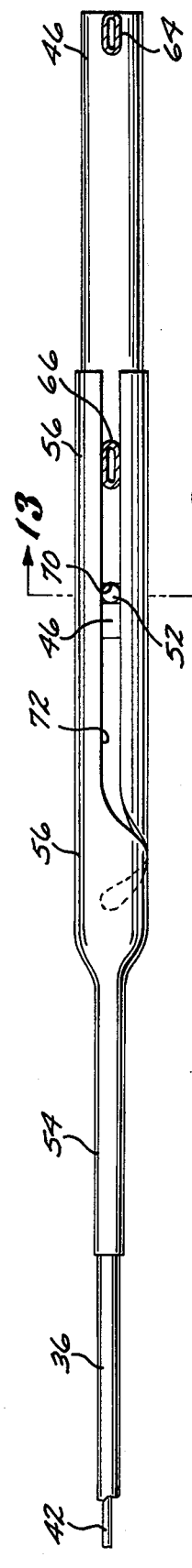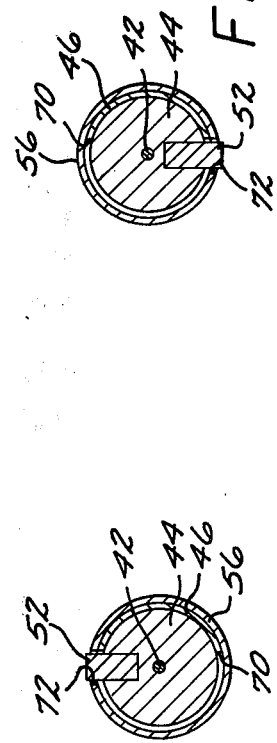

GAUGE FOR MEASURING LENGTH OF AN OPENING

BACKGROUND OF THE INVENTION

1. Field of the Invention

The present invention relates to a gauge for measuring the length of an opening, and more particularly to such a gauge operable with one hand and adapted for use where there is access to only one end of the opening.

2. Description of the Prior Art

There are a number of devices which are adapted to determine the length of an opening through an element where access can be had from only one end of the opening. However, most of these devices do not provide positive assurance that the gauge is firmly anchored in position upon the far edge of the opening prior to engagement of the near edge of the opening by another portion of the gauge. In the absence of this certainty of anchorage, the gauge can become disengaged from the far edge of the opening and provide an erroneous indication of the length of the opening.

Precise determination of the length of an opening is particularly important in surgical procedures. For example, in any operation requiring the use of bone screws for fixation of a fracture, either directly or through the use of adjunctive hardware such as metal plates, the exact length of the screws required must be determined. This cannot be measured directly because exposure to the bone opening is usually limited to one surface of the bone.

One prior device for measuring the proper length of screw in such a surgical procedure comprises a length of wire with a hook on one end and a sliding lock nut. The wire is inserted into the bone and the hook is engaged on the far edge or far outer cortex of the bone. The sliding member is brought to the near surface of the bone and tightened. Next, the wire is removed and the wire portion approximating the length of the opening is measured with an ordinary ruler. Such a procedure is cumbersome, requires the use of two hands, requires the use of a separate ruler, and is unreliable in that the wire often becomes bent and the hook is difficult to properly engage upon the far cortex of the bone.

SUMMARY OF THE INVENTION

According to the present invention, a gauge is provided for measuring the distance between the near and far edges of an elongated opening through an element, the gauge being particularly adapted for use in determining the proper length of screw to be utilized in an orthopaedic surgical operation involving internal fixation of a fracture.

The gauge comprises an elongated probe having a hook at its outer extremity adapted for location adjacent the far edge of the opening whose length is to be measured. The gauge further includes an elongated member which is longitudinally movable upon the probe toward the opening for engagement upon the near edge of the opening. The elongated member and probe include measurement means which cooperate to indicate the distance between those portions of the hook and elongated member in engagement with the opposite edges of the opening.

The gauge includes handle adapted to be held and squeezed with one hand to bring the probe and elongated member into operative position.

A mechanism is interposed between the probe and elongated member to effect secure engagement of the hook upon the far edge of the opening upon initial squeezing of the handle. Continued squeezing of the handle then brings the elongated member into engagement with the near edge of the opening. Further squeezing of the handle develops a slight compressive force to assure good engagement during a reading of the measurement means.

The length of the opening can be determined with access to only one end of the opening, the gauge is adapted to be operated with one hand, and there is a secure and reliable engagement of the hook upon the far edge of the opening so that the surgeon or other user can be substantially certain that the indication of the length of the opening is accurate.

One embodiment of the gauge includes a flexible element or linkage interposed between the handle means and the elongated member so that excessive squeezing of the handle means does not break any of the components, but simply resiliently flexes the flexible linkage.

In one embodiment of the present gauge, the probe includes a wire which carriers the hook at one end. The other end of the wire is attached to a cam member which cooperates with a cam track formed in the elongated member. This cooperation rotates the cam member, and the attached hook, upon initial movement of the elongated member upon the probe. Such rotation moves the hook laterally and into engagement with the far edge of the opening.

In another embodiment of the gauge, the diameter or size of the end of the probe having the hook is not sufficiently large to completely occupy the diameter or cross section of the opening whose length is to be determined. The probe is axially cocked to locate the hook in engagement with the far edge of the opening. Next, a longitudinally disposed rod on the probe is moved into position adjacent the hook to substantially fully occupy the adjacent portion of the opening, and thereby prevent lateral movement of the hook out of engagement with the far edge of the opening. To accomplish such movement of the rod, a cam member attached to one end of the rod cooperates with cam tracks provided in the probe and in the elongated member and the rod is moved during relative movement between the probe and the elongated member.

The measurement means displays the length of the opening directly or, for a particular application such as internal fixation in orthopaedic surgery, the measurement means can be calibrated to display the proper length of bone screw.

Other objects and features of the invention will become apparent from consideration of the following description taken in connection with the accompanying drawings.

BRIEF DESCRIPTION OF THE DRAWINGS

FIG. 1 is a side elevational view of one embodiment of a gauge according to the present invention;

FIG. 2 is a showing of the gauge of FIG. 1, with the probe inserted in an opening whose length is to be measured and with the handle shown in a compressed state;

FIG. 3 is a partial side-elevational view of the opposite side of the device of FIG. 2;

FIG. 4 is an enlarged detailed view of the probe in the opening whose length is to be measured, particularly illustrating engagement of the hook and elongated member with opposite edges of the opening;

FIG. 5 is a longitudinal cross sectional view of the probe and elongated member of FIG. 1;

FIG. 6 is an enlarged cross sectional view of the outer end portion of the probe of the device of FIG. 1;

FIG. 7 is a partial longitudinal cross sectional view of the outer extremity of the probe of FIG. 6, but illustrating the hook in its laterally displaced location;

FIG. 8 is a view taken along the line 8—8 of FIG. 6;

FIG. 9 is a view similar to FIG. 8, but illustrating the hook in the laterally disposed position of FIG. 7;

FIG. 10 is a partial bottom plan view of the inner extremities of the probe and elongated member;

FIG. 11 is a view similar to FIG. 10, but illustrating the elongated member in a projected position relative to the probe;

FIG. 12 is an enlarged view taken along the line 12—12 of FIG. 10;

FIG. 13 is an enlarged view taken along the line 13—13 of FIG. 11;

DESCRIPTION OF THE PREFERRED EMBODIMENT

Figure 14:
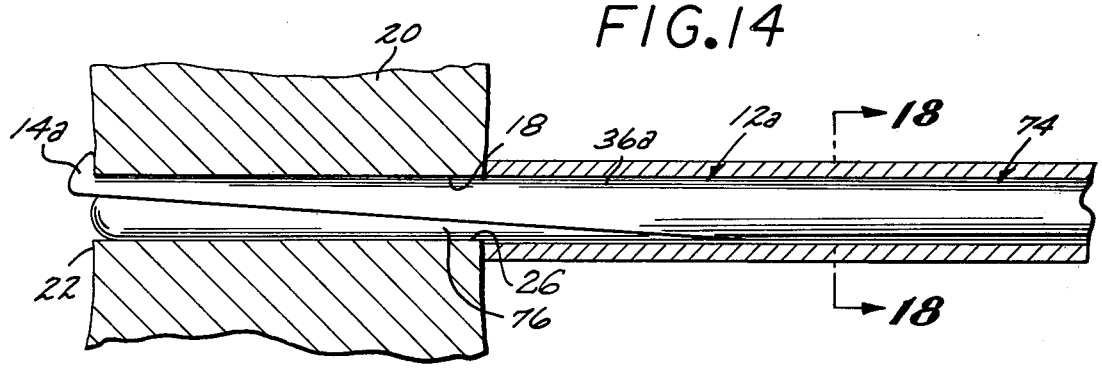
FIG. 14 is a partial side elevational view of another embodiment of the present invention, illustrating the probe components disposed within the opening whose length is to be measured.

Referring now to the drawings, two gauges will be described. Both are adapted for measurement of the length of an opening accessible from only one end, and both are particularly useful in surgical procedures such as operations by orthopaedic surgeons involving the use of bone screws for fixation of fractures. The drilled openings for the bone screws are of predetermined diameter, but require different lengths of bone screws, depending upon the length of the openings.

The probe of either gauge of the invention is insertable into the drilled bone opening and the proper length of screw for use with that opening is plainly indicated on a scale carried by the gauge when the handle of the gauge is squeezed. This squeezing causes portions of the gauge to engage the opposite, far and near edges of the bone opening and the extent of relative movement of these portions to effect such engagement is displayed as the depth of the opening. Secure engagement of the far edge of the opening is insured by providing a hook on the probe, and causing this hook to firmly seat upon the opening far edge upon initial squeezing of the gauge handle. In one embodiment the hook rotates into positive engagement with the far edge of the opening, and in another embodiment a rod slides up adjacent the probe hook to fill the drilled opening and prevent the hook from moving out of engagement with the far edge of the opening. In this regard, both gauges are used with drilled openings only slightly larger than the maximum diameter of the probe.

With particular reference to FIGS. 1 through 13, a gauge 10 constituting one embodiment of the invention is illustrated which comprises, generally, an elongated element 12 having a hook 14 at its outer extremity and an indicator means or scale 16 at its inner extremity. The probe outer extremity is adapted to be disposed through an opening 18 drilled or otherwise formed in the element or bone 20. The probe is inserted until the hook 14 is located approximately adjacent the far edge 22 defining the margin of the opening.

An elongated member 24 is longitudinally slidably carried by the probe 12 and is adapted for movement into engagement with the near edge 26 of the opening 18. The member 24 includes an indicator means or pointer 28 which is movable across the face of the scale 16 during movement of the member 24 relative to the probe 12. This displays the extent of relative movement and consequently the length of the opening 18.

A handle 30 includes handle parts 32 and 34 which are hinged together at the middle, and connected at the upper extremities to the probe 12 and member 24, respectively. Handle parts 32 and 34 are movable from the positions of FIG. 1 to those of FIG. 2 to effect compressive engagement of the hook 14 and member 24 upon the far and near opening edges 22 and 26.

As best seen in FIGS. 5 through 13, the probe 12 includes an elongated tube 36 which is slightly smaller in diameter than the diameter of the opening 18 in the bone 20. A plug 38 is fixed within the forward extremity of the tube 36, and includes an opening 40 located off-center with respect to the longitudinal axis of the plug 38. A wire 40 extends through the opening 40. This wire is relatively thin, such as about 0.0500 inches in diameter, and it is approximately three inchess long. The outer end of the wire 42 is welded or soldered to the hook 14. The hook 14 is generally hemispherical in configuration and overlies the end of the tube 36. When the wire 42 is rotated in the eccentrically located opening 40, the hook 14 is rotated from the position of FIG. 6 to that of FIG. 7. Rotation of the wire 42 is effected by rotation of a plug 44 to which the inner end of the wire 42 is welded or otherwise fixed. The plug 44 is located within a tubular sleeve 46 which constitutes a larger diameter inner portion of the tube 36. An elongated slot 48 is provided in the sleeve to facilitate its sterilization. As best seen in FIG. 5, the outer end of the sleeve 46 is closed by a centrally apertured end wall 50 to which the inner end of the tube 36 is welded or otherwise fixed.

The plug 44 includes a laterally extending pin or cam 52 which extends through slots or cam tracks provided in the sleeve 46 and member 24, as will be seen. Movement of the cam 52 through these cam tracks effects rotation of the plug 44, and consequently the wire 42 and hook 14, initial squeezing together of the handle parts 32 and 34.

The elongated member 24 includes two main portions, a tube 54 which longitudinally slidably receives the probe tube 36, and an inner, larger diameter sleeve 56 which slidably receives the probe sleeve 46. The sleeve 56 includes an elongated slot 58 to facilitate its sterilization.

The handle part 32 is pivotally connected at its upper end to the inner end to a flexible linkage or element 60 made of resilient material such as spring steel. The outer end of the element 60 is attached to a mounting tab 62 welded to the tube 54.

The other handle part 32 is upwardly bifurcated, one branch 64 being welded to the inner end of the probe sleeve 46 and to the scale 16, and the other branch 66 being welded to the scale 16 and to the outer end of the probe sleeve 46.

A pair of handle springs 68 are attached at their lower ends to the handle parts 32 and 34, respectively, and pivotally interengage at their upper ends. The springs 68 resiliently flex and tend to bias the handle parts 32 and 34 to the open position illustrated in FIG. 1. The springs 68 are deflectable to the positions illustrated in FIG. 2 upon squeezing together of the handle parts 32 and 34.

The resilience of the element 60 allows it to deflect upon over-squeezing of the handle parts 32 and 34, thus preventing breakage or failure of the hook 14 or the wire 42 which might occur if were an inflexible interconnection. Such an inflexible interconnection would allow tension to be developed in the wire 42 to such an extent that the hook 14 could possibly break off and fall into the area at the far side of the opening, which would be very undesirable in a surgical procedure.

As previously indicated initial squeezing together of the handle parts 32 and 34 rotates the hook 14 into engagement with the far edge 22 of the opening 18. This is accomplished by travel of the cam pine 52 through a circumferentially extending cam track 70 provided in the wall of the sleeve 46. The cam track 70 extends through approximately 180° of the wall circumference, and movement of the pine 52 through this 180° path causes movement of the hook 14 from the position illustrated in FIG. 6 to that of FIG. 7.

The cam pin 52 extends outwardly from the cam track 70 through another cam track 72 formed in the wall of the sleeve 56. As best seen in FIGS. 10 through 13, the outer end of the track 72 is located adjacent the outer end of the sleeve 56. From this point the track 72 extends helically rearwardly and downwardly to the underside of the sleeve 56, and then straight back or inwardly. The cam pin 52 is movable along the complete length of the cam track 72, as best seen in FIGS. 10 and 11, during relative movement between the sleeve 46 and 56. The upper end of the handle branch 66 is also slidable through this track 72 and constrains the sleeve 56 from rotating during its longitudinal movement relative to the probe sleeve 46.

In operation, the probe 12 is disposed within the opening 18 far enough to locate the hook 14 adjacent the opening far edge 22. The handle parts 32 and 34 are squeezed to advance the sleeve 56 over the probe sleeve 46. The initial relative movement brings the edges of the cam track 72 into engagement with the cam pin 52 and moves it downwardly and rearwardly along the helical path of the track 72. This rotates the cam pin 52 along the circumferential cam track 70, consequently rotating the wire 42 and hook 14. Rotation of the hook 14 brings it into the position illustrated in FIG. 3, in engagement with the far edge 22 with the opening 18.

Continued squeezing of the handle parts 32 and 34 advances the tube 54 toward the element 18 until it engages the near edge 26 of the opening 18. The degree of excursion of the member 24 relative to the probe 12, and thus the length of the opening 18, is indicated by the position of the pointer 28 relative to the scale 16. Any further squeezing of the handle parts 32 and 34 deflects the resilient element 60, rather than damaging the wire 42 or the hook 14. As a safety precaution the wire 42 is preferably diminished to a diameter of approximately 0.025 inches at its inner extremity, as best seen in FIG. 6, so that any failure of the wire will occur at that point. This leaves enough of the wire 42 projecting from the opening 18 to permit the broken off portion to be easily recovered from the near side of the opening 18.

Referring now to FIGS. 14 through 21, there is illustrated another embodiment of the invention, referred to for convenience as the gauge 74. It is identical to the gauge 10 in most respects and like numerals are employed to designate like parts. Where the parts are different but their functions are generally similar, a letter subscript is used.

The gauge 74 operates in substantially the same manner as the gauge 10 except that squeezing of the handle parts 32 and 34 is not effective to rotate a hook or the like. Instead, such squeezing moves an element into position adjacent the hook to fill the available space into which the hook might move for disengagement. More particularly, the gauge 74 includes a probe 12a having an integral, laterally extending tip or hook 14a. The probe diameter adjacent the hook 14a is substantially less than the predetermined diameter of the opening 18. This permits the probe 12a to be cocked or axially misaligned relative to the longitudinal axis of the opening 18 so that the hook 14a can be inserted into and through the opening 18. Once the hook 14a has passed beyond the far edge 22 of the opening 18, the probe 12a is then straightened or aligned with the longitudinal axis of the opening 18 to locate the hook 14a in the position illustrated in FIG. 14, in engagement with the opening far edge 22.

The probe 12a includes an elongated passage which longitudinally slidably receives an elongated rod 76. The rod 76 is normally located inwardly or to the right as viewed in FIG. 14. However, when the handle parts 32 and 34 are initially squeezed, the rod 76 slidably extends or moves longitudinally outwardly to the projected position illustrated in FIG. 14. In this position its diameter, combined with that of the adjacent end of the probe 12a, substantially completely fills the opening 18. This makes it impossible to cock or axially misalign the probe 12a sufficiently to move the hook 14a radially inwardly and out of engagement with the opening far edge 22.

Once the rod 76 is forwardly or outwardly projected, continued further squeezing of the handle parts 32 and 34 extends or brings the tube 54 into engagement with the opening near edge 26 in a manner identical to that described in connection with the previous embodiment.

Figure 15:
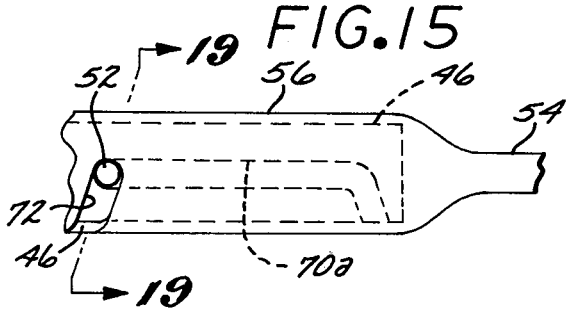
FIG. 15 is an enlarged partial side elevational view of the side of the device opposite that illustrated in FIG. 14.
Figure 16:
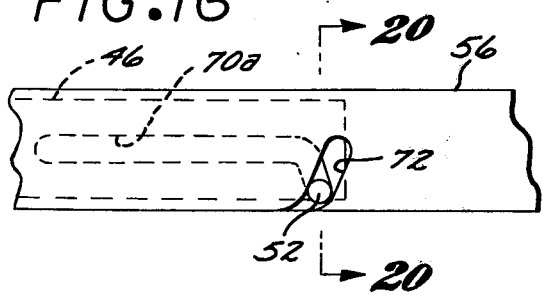
FIG. 16 is a view similar to FIG. 15, illustrating the location of the gauge components after initial extension or projection of the elongated member upon the probe.
Figure 17:
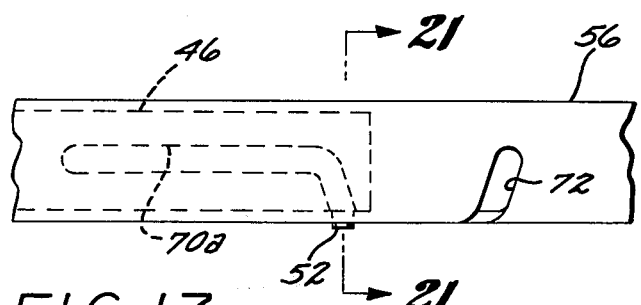
FIG. 17 is a view similar to FIG. 16, but illustrating the elongated member in a still more projected position relative to the probe.
Figure 18:
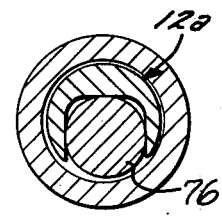
FIG. 18 is an enlarged view taken along the line 18—18 of FIG. 14.
Figure 19:
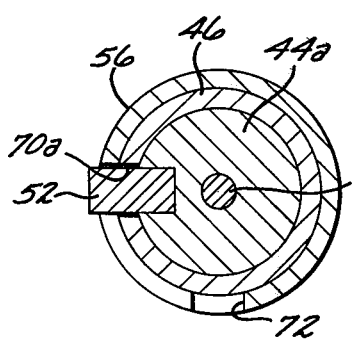
FIG. 19 is an enlarged view taken along the line 19—19 of FIG. 15.
Figure 20:
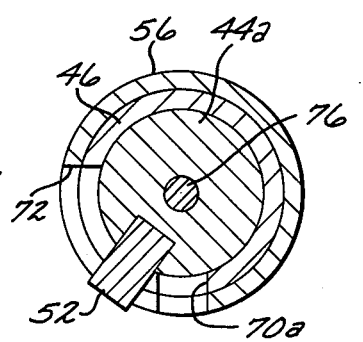
FIG. 20 is an enlarged view taken along the line 20—20 of the FIG. 16.
Figure 21:
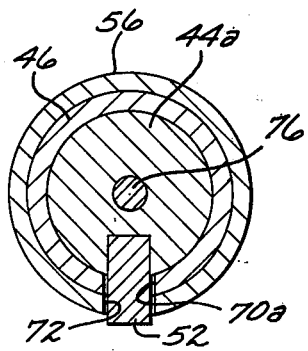
FIG. 21 is an enlarged view taken along the line 21—21 of FIG. 17.

The outer extremity of the sleeve 56 includes a cam track 70a having a circumferentially directed outer portion and a longitudinally extending inner portion, as best seen in FIG. 15. A cam pin 52 extends radially outwardly through the cam track 70a and also through the cam track 72 in sleeve 56. As a consequence, the sides of the helical portion of the cam track 72 are coupled to and thereby engage and move the cam pin 52 outwardly along the length of the cam track 70a, accompanied by corresponding outward movement of the rod 76. This continues until the rod 76 is disposed adjacent the hook 14a in the position illustrated in FIG. 14. At this point the cam pin 52 is urged by the sides of the cam track 72 into the circumferential portion of the cam track 70a, thereby effecting decoupling the rod 76 from the member 24 halting further outward movement of the rod 76. The circumferential portion of the track 70a generally coincides with the helical portion of the track 72 so that the cam pin 52 moves into the longitudinal portion of the track 70. This allows outward movement of the member 24 as the handle parts 32 and 34 are further squeezed, but without accompanying movement of the rod 76.

The handle parts 32 and 34 are squeezed until a slight compressive force is developed between the hook 14a and the outer end of the member tube 54, and the correct length of the opening 18 is then displayed on the scale 16, as previously described in connection with the gauge 10.

The rod 76 is sufficiently stronger than the wire 42 and hook 14 combination that a rigid linkage or element could be used instead of the flexible element 60, if desired.

From the foregoing it will be apparent that the gauges of the present invention provide an easily operable means for determining the length of an opening from only one end. Engagement of the gauge components with the near and far edges of the opening reliable and secure, and the operation is easily accomplished using only one hand.

Various modifications and changes may be made with regard to the foregoing detailed description without departing from the spirit of the invention.

I claim:

1. A gauge for measuring the distance between the near and far edges of an elongated opening through an element, said gauge comprising:
   a rigid elongated probe including an outer extremity having a hook and an inner extremity having a first indicator means, said hook being engageable upon the far edge of the opening upon disposition of said outer extremity through the opening in the element;
   an elongated member longitudinally extensible alongside said probe for engagement upon the near edge of the opening, said member including a second indicator means cooperative with said first indicator means to indicate the distance between the portions of said hook and said member in engagement with said far and near edges, respectively, to thereby indicate the length of the opening;
   an elongated rod coupled to said member and extensible therewith to a projected position upon initial extension of said member, said rod having an outer extremity located adjacent said hook in said projected position to substantially fill said opening and prevent disengagement between said hook and said far edge; and
   handle means connected to said probe and to said member and operative to effect relative longitudinal movement therebetween.

2. A gauge according to claim 1 and including decoupling means operative upon location of said outer extremity of said rod adjacent said hook to decouple said rod and said member whereby said member is extensible independently of said rod.

3. A gauge according to claim 2 wherein said decoupling means comprises a first cam track in said probe; a second cam track in said member; and a cam member carried by said rod and projecting into said first and second cam tracks, said cam member being engageable by said elongated member, whereby said rod and said elongated member are initially extensible together, said cam member being engageable by said probe for movement through said second track upon location of said rod outer extremity in said projected position, whereby further extension of said elongated member is independent of said rod.

4. A gauge according to claim 1 wherein said probe includes an elongated passage, and said rod is longitudinally slidable within said passage.

5. A gauge according to claim 1 wherein said first indicator means comprises a scale and said second indicator means comprises a point movable across said scale upon relative movement between said probe and said elongated member.

6. A gauge for measuring the distance between the near and far edges of a cylindrical opening through an element, said gauge comprising:
   an elongated probe of predetermined cross section having an inner extremity and an outer extremity, and including an elongated passage terminating inwardly of said outer extremity to define a probe outer portion smaller than said predetermined cross section, said probe further including a laterally extending hook at said outer extremity, said outer extremity being rigid for engagement of said hook upon the far edge of the opening upon disposition of said extremity through the opening in the element;
   an elongated tubular member slidably receiving said probe and longitudinally extensible along said probe for engagement upon the near edge of the opening;
   measurement means on said probe and said member operative to display the extent of relative movement therebetween whereby the distance between the portions of said hook and said member in engagement with said far and near edges, respectively, and consequently the length of said opening, can be determined;
   an elongated rod slidable within said elongated passage of said probe, said rod being coupled to and extensible with said member to a projected position upon initial extension of said member, said rod having an outer extremity located adjacent said probe outer portion in said projected position to define a cross section approximating said predetermined cross section of said probe for preventing disengagement of said hook from the far edge of the opening;
   handle means connected to said probe and to said member and operative to effect relative slidable movement therebetween; and
   means operative upon location of said outer extremity of said rod in said projected position to decouple said rod and said member whereby said member is extensible independently of said rod.

7. A gauge according to claim 6 wherein said last-mentioned means comprises a first cam track in said probe; a second cam track in said member; and a cam member carried by said rod and projecting into said first and second cam tracks, said cam member being engageable by said elongated member for movement through said first cam track upon initial extension of said member, whereby said rod and said elongated member are initially extensible together, said cam member being engageable by said probe for movement through said second track upon location of said rod outer extremity in said projects position, whereby further extension of said elongated member is independent of said rod.

8. A gauge according to claim 7 wherein said cam member is engageable by said probe, upon location of said rod outer extremity in said projected position, to constrain said rod against longitudinal movement relative to said probe.

* * * * *